(12) United States Patent
Eom et al.

(10) Patent No.: US 11,883,166 B2
(45) Date of Patent: Jan. 30, 2024

(54) APPARATUS AND METHOD FOR ESTIMATING COMPONENT OF ANALYTE

(71) Applicant: SAMSUNG ELECTRONICS CO., LTD., Suwon-si (KR)

(72) Inventors: Kun Sun Eom, Yongin-si (KR); Sang Kyu Kim, Yongin-si (KR); Yoon Jae Kim, Seoul (KR); Hyun Seok Moon, Hwaseong-si (KR); Jin Young Park, Hwaseong-si (KR); Sung Mo Ahn, Yongin-si (KR); Myoung Hoon Jung, Bucheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 381 days.

(21) Appl. No.: 17/185,432

(22) Filed: Feb. 25, 2021

(65) Prior Publication Data
US 2022/0167883 A1 Jun. 2, 2022

(30) Foreign Application Priority Data

Nov. 30, 2020 (KR) ........................ 10-2020-0164184

(51) Int. Cl.
| A61B 5/1455 | (2006.01) |
| A61B 5/1495 | (2006.01) |
| A61B 5/00 | (2006.01) |
| A61B 5/145 | (2006.01) |

(52) U.S. Cl.
CPC .......... *A61B 5/1455* (2013.01); *A61B 5/1495* (2013.01); *A61B 5/7278* (2013.01);
(Continued)

(58) Field of Classification Search
CPC .............. A61B 5/1455; A61B 5/14551; A61B 5/14552; A61B 5/1495; A61B 5/7278;
(Continued)

(56) References Cited

U.S. PATENT DOCUMENTS 5,036,311 A 7/1991 Moran et al.
9,463,333 B2 10/2016 Wagenaar Cacciola et al.
(Continued)

FOREIGN PATENT DOCUMENTS

KR 10-2007-0092169 A 9/2007
KR 10-2020-0020671 A 2/2020
KR 10-2020-0077052 A 6/2020

OTHER PUBLICATIONS

Communication dated Dec. 23, 2021 by the European Patent Office for European Patent Application No. 21184561.5.
(Continued)

*Primary Examiner* — Eric F Winakur
(74) *Attorney, Agent, or Firm* — Sughrue Mion, PLLC

(57) ABSTRACT

An apparatus for estimating a component of an analyte may include a sensor including a light source configured to emit light to the analyte, and a detector configured to measure a spectrum of light reflected from the analyte; and a processor configured to: based on an initial amount of received light being obtained from the analyte by operating the sensor under initial operating conditions, determine optimal operating conditions based on the initial amount of received light and the initial operating conditions; and based on a spectrum being measured from the analyte by operating the sensor under the optimal operating conditions, estimate the component of the analyte based on the spectrum.

31 Claims, 16 Drawing Sheets

(52) U.S. Cl.
CPC ............ *A61B 5/742* (2013.01); *A61B 5/7405* (2013.01); *A61B 5/14532* (2013.01); *A61B 5/14546* (2013.01); *A61B 5/443* (2013.01); *A61B 5/681* (2013.01); *A61B 5/6803* (2013.01); *A61B 5/6898* (2013.01)

(58) Field of Classification Search
CPC ... A61B 5/7405; A61B 5/742; A61B 5/14532; A61B 5/14546; A61B 5/443; A61B 5/6803; A61B 5/681; A61B 5/6898
See application file for complete search history.

(56) References Cited

U.S. PATENT DOCUMENTS

| | | | |
|---|---|---|---|
| 10,433,738 | B2 | 10/2019 | Vermeulen et al. |
| 2002/0038080 | A1 | 3/2002 | Makarewicz et al. |
| 2007/0213694 | A1 | 9/2007 | Perl et al. |
| 2010/0179622 | A1 | 7/2010 | Wagenaar Cacciola et al. |
| 2015/0109617 | A1 | 4/2015 | Gilbert et al. |
| 2016/0097716 | A1 | 4/2016 | Gulati et al. |
| 2018/0056088 | A1 | 3/2018 | Moffat |
| 2018/0066984 | A1 | 3/2018 | Rastegar et al. |
| 2020/0029873 | A1 | 1/2020 | Park et al. |
| 2020/0069225 | A1 | 3/2020 | Vizbaras et al. |
| 2020/0138349 | A1* | 5/2020 | Lamminmaki .... A61B 5/14552 |
| 2020/0196935 | A1 | 6/2020 | Eom et al. |

OTHER PUBLICATIONS

Tanja M. Greve et al., "Penetration mechanism of dimethyl sulfoxide in human and pig ear skin: An ATR-FTIR and near-FT Raman spectroscopic in vivo and in vitro study", Spectroscopy, 22, DOI 10.3233/SPE-2008-0358, IOS Press, 2008, pp. 405-417, 14 pages total.

* cited by examiner

APPARATUS AND METHOD FOR ESTIMATING COMPONENT OF ANALYTE

CROSS-REFERENCE TO RELATED APPLICATION(S)

This application is based on and claims priority under 35 U.S.C. § 119 to Korean Patent Application No. 10-2020-0164184, filed on Nov. 30, 2020, in the Korean Intellectual Property Office, the disclosure of which is incorporated by reference herein in its entirety.

BACKGROUND

1. Field

The disclosure relates to an apparatus and method for estimating a component of an analyte based on a dynamic range.

2. Description of Related Art

Reactive oxygen species are an important part of the biological defense mechanisms, such as white blood cells that protect the body against infections. However, it has been known that excessive production of reactive oxygen species in the body may lead to various diseases in tissues. Common factors that cause the reactive oxygen species include stress, alcohol, peroxides, medicine, and the like. The reactive oxygen species produced by these factors may cause cranial nerve diseases, circulatory diseases, cancer, digestive tract diseases, liver diseases, arteriosclerosis, renal diseases, diabetes, aging, and the like. Human bodies have a series of antioxidant defense systems to protect against oxygen toxicity. In order for such systems to normally operate, sufficient amounts of antioxidants are needed such as vitamin E, vitamin C, carotenoid, flavonoid, and the like. Thus, there is a need for an apparatus and a method for easily identifying the amount of antioxidants in the body.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an example embodiment, an apparatus for estimating a component of an analyte may include a sensor including a light source configured to emit light to the analyte, and a detector configured to measure a spectrum of light reflected from the analyte; and a processor configured to: based on an initial amount of received light being obtained from the analyte by operating the sensor under initial operating conditions, determine optimal operating conditions based on the initial amount of received light and the initial operating conditions; and based on a spectrum being measured from the analyte by operating the sensor under the optimal operating conditions, estimate the component of the analyte based on the spectrum.

The initial operating conditions of the sensor may include at least one of an intensity of incident light, a gain, an exposure time, or an aperture size.

The initial operating conditions may be set such that a preset optimal amount of received light is detected from a standard sample having a predetermined reflectivity.

The predetermined reflectivity may include at least one of an average reflectivity and a maximum reflectivity of the analyte.

The processor may be further configured to determine the optimal operating conditions based on a ratio of the initial amount of received light to a preset optimal amount of received light and the initial operating conditions.

The processor may be further configured to change the optimal operating conditions to a first threshold based on the optimal operating conditions being less than the first threshold.

The processor may be further configured to change the optimal operating conditions to a second threshold based on the optimal operating conditions exceeding the second threshold.

The processor may be further configured to, based on the optimal operating conditions exceeding the second threshold, repeatedly obtain an initial amount of received light by operating the sensor after increasing a light source current among the initial operating conditions.

The apparatus may include a force sensor or a pressure sensor configured to measure a force or a pressure applied between the analyte and the sensor. The processor may be further configured to operate the sensor based on the force or the pressure being greater than or equal to a predetermined threshold.

The processor may be further configured to control an output interface to output information that guides a user to change the force or the pressure applied between the analyte and the sensor based on the force or the pressure.

The processor may be further configured to obtain an absorption spectrum of the analyte based on the spectrum and a reference spectrum.

The processor may be further configured to obtain the reference spectrum by normalizing a sample spectrum measured using a standard sample having a predetermined reflectivity based on the initial operating conditions and the optimal operating conditions.

The processor may be further configured to normalize the spectrum by multiplying an amount of reflected light of the sample spectrum by a ratio of an exposure time among the optimal operating conditions and an exposure time among the initial operating conditions.

The processor may be further configured to obtain the reference spectrum that corresponds to the optimal operating conditions by referring to a preset lookup table.

The processor may be further configured to estimate the component of the analyte based on the absorption spectrum by using a preset estimation model.

The component of the analyte may include at least one of skin carotenoid, blood carotenoid, glucose, urea, lactate, triglyceride, total protein, cholesterol, or ethanol.

According to an aspect of an example embodiment, a method of estimating a component of an analyte may include operating a sensor under preset initial operating conditions; detecting an initial amount of received light from the analyte under the initial operating conditions; determining optimal operating conditions based on the initial amount of received light and the initial operating conditions; measuring a spectrum from the analyte by operating the sensor under the optimal operating conditions; and estimating the component of the analyte based on the spectrum.

The initial operating conditions may be set such that a preset optimal amount of received light is detected from a standard sample having a predetermined reflectivity.

The determining of the optimal operating conditions may include determining the optimal operating conditions based on a ratio of the initial amount of received light to a preset optimal amount of received light and the initial operating conditions.

The determining of the optimal operating conditions may include changing the optimal operating conditions to a first threshold based on the determined optimal operating conditions being less than the first threshold.

The determining of the optimal operating conditions may include changing the optimal operating conditions to a second threshold based on the determined optimal operating conditions exceeding the second threshold.

The determining of the optimal operating conditions may include, based on the determined optimal operating conditions exceeding the second threshold, repeatedly obtaining an initial amount of received light by operating the sensor after increasing a light source current among the initial operating conditions.

The method may include measuring a force or a pressure applied between the analyte and the sensor. The operating of the sensor under the initial operating conditions may include operating the sensor based on the measured is the force or the pressure being greater than or equal to a predetermined threshold.

The obtaining of the component of the analyte may include obtaining a reference spectrum, obtaining an absorption spectrum of the analyte based on the spectrum and the reference spectrum, and estimating the component of the analyte based on the absorption spectrum.

The obtaining the reference spectrum may include obtaining the reference spectrum by normalizing a sample spectrum measured using a standard sample having a predetermined reflectivity based on the initial operating conditions and the optimal operating conditions.

The obtaining the reference spectrum may include obtaining the reference spectrum that corresponds to the optimal operating conditions by referring to a preset lookup table.

The estimating of the component may include estimating the component of the analyte based on the absorption spectrum by using a preset estimation model.

According to an aspect of an example embodiment, an electronic device may include a main body; a memory disposed in the main body; and a processor disposed in the main body and electrically connected to the memory. The processor may be configured to operate a sensor device under initial operating conditions stored in the memory based on a request for estimating an antioxidant index being received, adjust, based on an initial amount of received light being obtained from skin of a user, at least one of a light exposure time and a light source current among operating conditions of the sensor device based on the initial amount of received light, obtain a spectrum from skin of the user by operating the sensor device under adjusted operating conditions, and estimate the antioxidant index based on the spectrum.

The electronic device may include at least one of a smart watch, a smart band, smart glasses, a smart earphone, a smart ring, a smart patch, a smart necklace, or a smartphone.

The processor may be further configured to set the initial operating conditions such that a preset optimal amount of received light is detected from a standard sample having a predetermined reflectivity.

The processor may be configured to adjust the light exposure time based on a ratio of the initial amount of received light to a preset optimal amount of received light and the light exposure time of the initial operating conditions.

The processor may be further configured to, based on an adjusted light exposure time being less than a first threshold, change the light exposure time to the first threshold, and based on the adjusted light exposure time exceeding a second threshold, change the light exposure time to the second threshold, or repeatedly obtain the initial amount of received light and adjust operating conditions of a light source after increasing the light source current.

The electronic device may include an output interface, disposed in the main body, including at least one of a sound module and a display that outputs a processing result of the processor.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
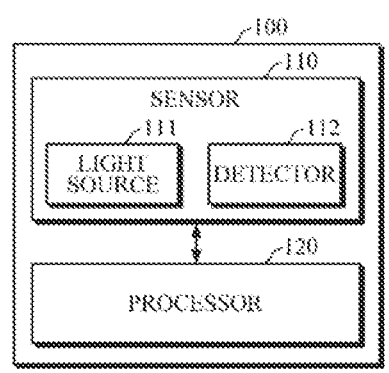
FIG. 1 is a block diagram illustrating an apparatus for estimating a component according to an example embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of exemplary embodiments are provided in the following detailed description with reference to the accompanying drawings. The disclosure may be understood more readily by reference to the following detailed description of exemplary embodiments and the accompanying drawings. The disclosure may, however, be embodied in many different forms and should not be construed as being limited to the embodiments set forth herein. Rather, these embodiments are provided so that the disclosure will be thorough and complete and will fully convey the concept of the invention to those skilled in the art, and the disclosure will only be defined by the appended claims. Like reference numerals refer to like elements throughout the specification.

It will be understood that, although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. In the specification, unless explicitly described to the contrary, the word "comprise," and variations such as "comprises" or "comprising," will be understood to imply the inclusion of stated elements but not the exclusion of any other elements. Terms such as "unit" and "module" denote units that process at least one function or operation, and the units may be implemented by using hardware, software, or a combination of hardware and software.

Hereinafter, various embodiments of an analyte concentration estimation apparatus and method will be described in detail with reference to the drawings.

Figure 2A:
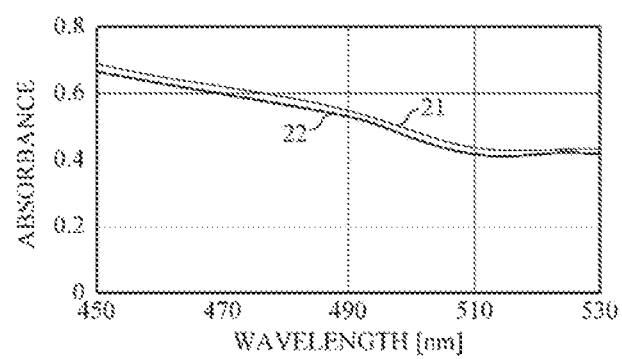
FIGS. 2A and 2B are diagrams for explaining the influence of a spectrum according to varying of operating conditions.
Figure 2B:
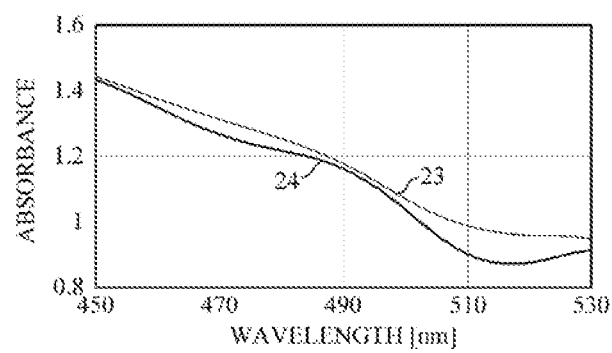
Figure 3:
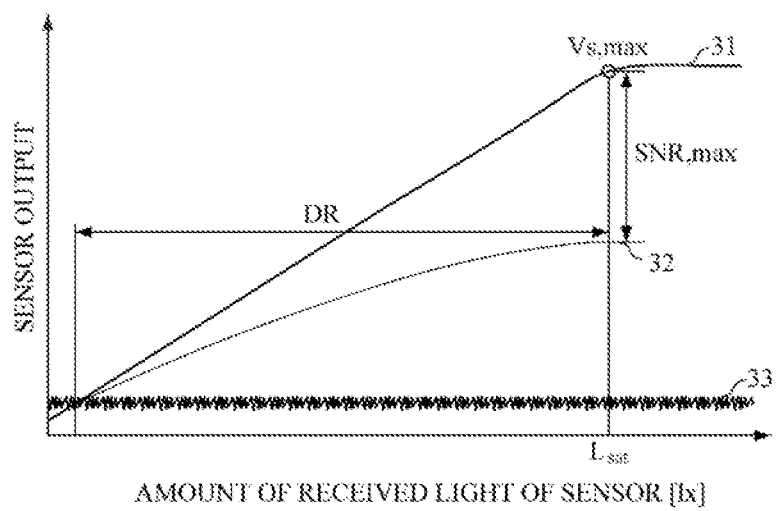
FIG. 3 is a diagram for explaining adjustment of operating conditions of a sensor.

FIG. 1 is a block diagram illustrating an apparatus for estimating a component of an analyte according to an example embodiment. FIGS. 2A and 2B are diagrams for explaining the influence of a spectrum according to varying of operating conditions. FIG. 3 is a diagram for explaining adjustment of operating conditions of a sensor.

Referring to FIG. 1, an apparatus 100 for estimating a component of an analyte includes a sensor 110 and a processor 120.

The sensor 110 may measure a spectrum for estimating a component of an analyte. In this case, the analyte may be a human skin tissue. For example, the analyte may include a palm or sole in which an epidermal layer is thick, an area in which venous blood or capillary blood is located or which is adjacent to the radial artery, and other peripheral parts of the human body, such as fingers, toes, or earlobes, which are areas with high blood vessel density, and an area that may be in contact with a wearable device when worn, such as a wrist, an inner ear, or the like, and an appropriate measurement position may be selected according to a component of an analyte to be estimated.

A light source 111 may include one or more light emitters. In this case, the light emitter may include a light emitting diode, a laser diode, a phosphor, and the like, but is not limited thereto. The one or more light emitters may be configured to emit light of different wavelengths. For example, the light source 111 may include an absorption band of an antioxidant substance (e.g., carotenoid) such as, for example, a wavelength band of 420 nm to 510 nm.

A detector 112 may include a photodiode, a phototransistor, or the like, or may be configured by a spectrometer, a waveguide connected to an external spectrometer, or the like. However, the detector 112 is not limited thereto, and may be formed by a complementary metal-oxide semiconductor (CMOS) image sensor, a charge-coupled device (CCD) image sensor, or the like. The detector 112 may receive light scattered or reflected from the analyte, convert the received light into an electrical signal, and output the electrical signal.

In addition, the sensor 110 may include an analog-to-digital converter for converting the electrical signal output from the detector 112 into a digital signal and/or an amplifier for amplifying the electrical signal.

The processor 120 may control the sensor 110 to obtain a spectrum from the analyte. The processor 120 may adaptively adjust operating conditions of the sensor 110 when the sensor 110 measures a spectrum from the analyte. In this case, the operating conditions of the sensor 110 may be variable, and may include parameters such as, for example, an intensity of incident light from a light source, a gain, a light exposure time, an aperture size, and the like. The sensor 110 according to the present embodiment may be formed to have a limited dynamic range. For example, a virtual dynamic region may be secured through varying of an exposure time, thereby securing sensing performance even in a skin tissue with low reflectivity.

For example, FIG. 2A shows spectra measured in a range (e.g., 28.2%) in which the reflectivity is relatively high where linearity is maintained. It can be seen that linearity is maintained in both a spectrum 22 obtained by fixing the operating conditions of the sensor and a spectrum 21 obtained by varying the operating conditions such as, especially, the exposure time. Further, FIG. 2B shows spectra measured in a range (e.g., 6.6%) in which the reflectivity is relatively low where linearity is not maintained. It can be seen that linearity is not maintained in a spectrum 24 obtained by fixing the operating conditions of the sensor whereas linearity is maintained in a spectrum 23 obtained by varying the light exposure time.

The processor 120 may operate the sensor 110 by using predefined initial operating conditions, and when the sensor 110 acquires data on an initial amount of received light from the analyte according to the initial operating conditions, determine optimal operating conditions using the acquired data. Then, the processor 120 may acquire a spectrum from the analyte by operating the sensor 110 according to the determined optimal operating conditions. The processor 120 may operate the light source 111 of the sensor 110 at a point in time at which a predetermined pressure is applied to the analyte while the analyte is in contact with the sensor 110.

The processor 120 may set the initial operating conditions using a standard sample having a predetermined reflectivity such as, for example, the average reflectivity (e.g., about 50%) or maximum reflectivity (about 80%) of human skin. For example, the processor 120 may set operating conditions that allow an optimal amount of received light to be obtained from the standard sample having a predetermined reflectivity, as the initial operating conditions.

FIG. 3 shows a signal 31 output by being converted into an electrical signal relative to the detected amount of received light, a signal of signal-dependent noise 32, and a signal of signal-independent noise 33. As shown, the output signal 31 of the detector 112 is saturated near the maximum value $V_{s,max}$. The amount of light received at this point can be the maximum amount $L_{sat}$ of light that can be received, and a signal-to-noise ratio (SNR) becomes the maximum. In this case, referring to Equation 1 below, the optimal amount $L_{opt}$ of received light is set within the dynamic range (DR), wherein a predefined value a may be multiplied to approach the maximum amount $L_{sat}$ of received light and a predetermined difference b may be reflected by taking into account that the measurements are made with a time difference.

$$L_{opt}=aL_{sat}-b \quad \text{Equation (1)}$$

When receiving a request for estimating an analyte, the processor 120 may operate the light source 111 of the sensor 110 to emit light to the analyte by using the initial operating conditions which are preset using the standard sample as described above, and may obtain the initial amount of received light from the analyte through the detector 112. When the initial amount of received light is obtained from the analyte, the processor 120 may determine the optimal operating conditions using the initial operating conditions, an optimal amount of received light, and data on the initial amount of light received. Equation 2 below is an example of an equation for obtaining an optimal exposure time among the optimal operating conditions.

$$\frac{L_{opt}}{L_{init}} = \frac{T_{opt}}{T_{init}} \quad (2)$$

Here, $L_{opt}$ denotes an optimal amount of received light, and $L_{limit}$ denotes the initial amount of received light obtained from an analyte. $T_{opt}$ denotes a light exposure time of optimal operating conditions to be obtained, and $T_{limit}$ denotes a light exposure time of initial operating conditions. As shown in the example, the processor 120 may determine an optimal exposure time through a relationship between a ratio of the optimal amount of received light and the initial amount of received light and a ratio of the optimal exposure time and the initial exposure time.

When the optimal operating conditions are determined as described above, the processor 120 may compare the determined optimal operating conditions with a range between a first threshold and a second threshold, and adjust the optimal operating conditions based on the determined optimal operating conditions being outside of the range. In this case, the first threshold may be set on the basis of an exposure time at the time of measuring a sample with a maximum predictable reflectivity (e.g., 80%), and the second threshold may be set on the basis of a smaller value of an exposure time at the time of measuring a sample with a minimum predictable reflectivity (e.g., 5%) and a maximum exposure time that can be set in consideration of a total exposure time (e.g., 5 seconds). However, the embodiment is not limited thereto.

For example, the processor 120 may not change the optimal exposure time when the optimal exposure time is greater than or equal to the first threshold and less than or equal to the second threshold, and when the optimal exposure time exceeds the second threshold, the processor 120 may change the second threshold to the optimal exposure time.

In another example, the processor 120 may change the first threshold to the optimal exposure time when the determined optimal exposure time is less than the first threshold. When the optimal exposure time exceeds the second threshold, the processor 120 may adjust the intensity of incident light by increasing a light source driving current among the initial operating conditions and then may repeatedly perform the process of obtaining the initial amount of received light by operating the light source according to the adjusted current. Here, the processor 120 may omit the process of comparing the optimal operating conditions and the first threshold. For example, in a case where the optimal operating condition is set to a value obtained at the time of the maximum skin reflectivity, the optimal exposure time may always exceed the first threshold when the first threshold is set as described above, and hence the process of comparing the optimal operating conditions and the first threshold can be omitted.

When the optimal exposure time is determined as described above, the processor 120 may obtain a spectrum from the analyte by operating the sensor 110 according to the optimal operating conditions in which the initial exposure time in the initial operating conditions is changed to the optimal exposure time. When the measured spectrum is received from the sensor 110, the processor 120 may analyze the received spectrum to estimate a component of the analyte. In this case, the component of the analyte may be an antioxidant index including skin carotenoid and/or blood carotenoid. However, the component of the analyte is not limited thereto, and a component, such as glucose, urea, lactate, triglyceride, total protein, cholesterol, or ethanol, may be estimated.

For example, when the spectrum is measured from the analyte by the sensor 110 according to the optimal operating conditions, the processor 120 may obtain an absorption spectrum using the measured spectrum and a reference spectrum. The processor 120 may normalize the spectrum measured using a standard sample having a predetermined reflectivity into an exposure time of operating conditions to obtain the reference spectrum. Equation 3 below is an example of an equation for obtaining a reference spectrum.

$$I_{ref} = I_{init} \times \frac{T_{opt}}{T_{init}} \quad \text{Equation (3)}$$

Here, $I_{ref}$ denotes a reference spectrum to be obtained. $I_{init}$ denotes a spectrum measured using a standard sample having a predetermined reflectivity such as, for example, the average reflectivity (about 50%) or maximum reflectivity (about 80%) of human skin. $T_{opt}$ denotes an exposure time of optimal operating conditions, and $T_{init}$ denotes an exposure time of initial operating conditions.

Alternatively, the processor 120 may obtain the absorbance of each wavelength corresponding to the optimal exposure time by referring to a lookup table that defines the absorbance of each wavelength for each exposure time, and obtain the reference spectrum through the obtained absorbance. In this case, the lookup table may be predefined by measuring the absorbance of each wavelength for each exposure time using the standard sample having a predetermined reflectivity. However, the lookup table is not limited thereto.

Also, when the reference spectrum is obtained as described above, the processor 120 may obtain an absorption spectrum using the reference spectrum and the spectrum obtained by the sensor 110 according to the optimal operating conditions. Equation 4 below is an example of an equation for obtaining an absorption spectrum.

$$A_s = -\log_{10}\left(\frac{I_s}{I_{ref}}\right) \quad \text{Equation (4)}$$

Here, $A_s$ denotes an absorption spectrum, $I_s$ denotes a spectrum measured from an analyte under optimal operating conditions, and $I_{ref}$ denotes a reference spectrum.

When the absorption spectrum of the analyte is obtained as described above, the processor 120 may estimate a component of the analyte using the obtained absorption spectrum. In this case, the processor 120 may estimate the component on the basis of the absorption spectrum by using a component estimation model that is predefined through a correlation between the absorbance of the absorption spectrum and the component to be estimated. The component estimation model may be defined as a linear or nonlinear functional equation and may be predefined through deep learning, artificial intelligence, or the like.

As described above, the processor 120 may repeatedly perform the process of obtaining the initial amount of received light from the analyte under the initial operating conditions and the process of obtaining a spectrum from the analyte under the optimal operating conditions and obtaining the absorption spectrum using the obtained spectrum multiple times. When a plurality of absorption spectra are obtained as described above, the processor 120 may estimate the component of the analyte by averaging all of the obtained absorption spectra, averaging the obtained absorption spectra after removing abnormal spectra, or selecting one optimal absorption spectrum, in order to reduce errors caused by blood or skin movement.

Figure 4:
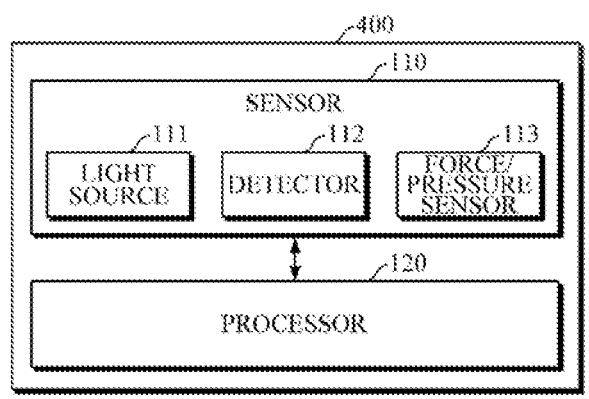
FIG. 4 is a block diagram illustrating an apparatus for estimating a component according to another example embodiment.

FIG. 4 is a block diagram illustrating an apparatus for estimating a component of an analyte according to another example embodiment.

Referring to FIG. 4, an apparatus 400 for estimating a component includes a sensor 110 and a processor 120. The sensor 110 may include a light source 111, a detector 112, and a force/pressure sensor 113. The light source 111, the detector 112, and the processor 120 are described above, and hence a description will be made with a focus on configurations that are not redundant.

The force/pressure sensor 113 may measure force/pressure that an analyte in contact with the sensor 110 applies to the sensor 110. The force/pressure sensor 113 may include a force sensor, a force sensor array, a contact pressure sensor, or a combination of an area sensor and a force sensor. For example, the force/pressure sensor 113 may be a voltage-resistive force sensor, an ultrasonic force sensor, a load cell sensor, a capacitive force sensor, a pyroelectric force sensor, a strain gauge type force sensor, an electrochemical force sensor, an optical force sensor, or a magnetic force sensor.

The processor 120 may be connected to the force/pressure sensor 113 and receive a value of a force/pressure between an analyte and the sensor 110 from the force/pressure sensor 113, and may operate the light source 111 of the sensor 110 under the initial operating conditions as described above when the received value of the force/pressure is greater than or equal to a preset threshold. In addition, the processor 120 may control an output interface to output information to guide a user to apply an appropriate pressure to the sensor 110 during the measurement time based on the force/pressure measured through the force/pressure sensor 113. In this case, guide information may be provided to the user through an output interface mounted on the apparatus 400 for estimating a component or an output interface of a connected external device.

Figure 5:
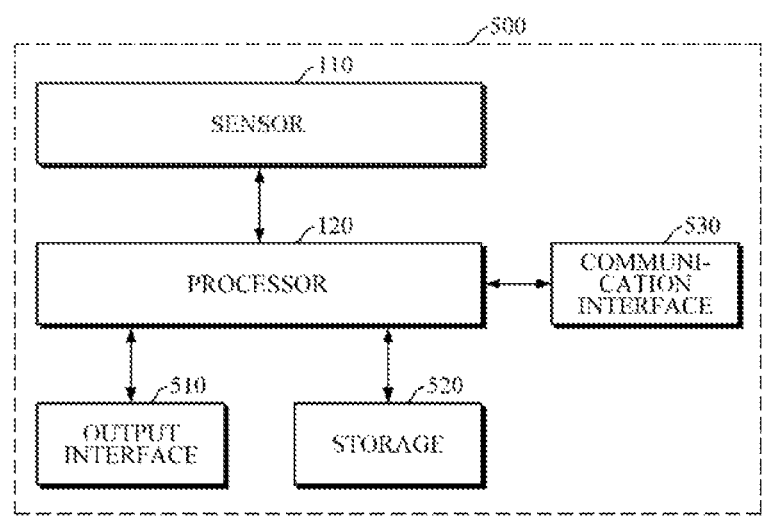
FIG. 5 is a block diagram illustrating an apparatus for estimating a component according to still another example embodiment.

FIG. 5 is a block diagram illustrating an apparatus for estimating a component according to still another example embodiment.

Referring to FIG. 5, an apparatus 500 for estimating a component may include a sensor 110, a processor 120, an output interface 510, a storage 520, and a communication interface 530. The sensor 110 and the processor 120 are described above, and hence descriptions thereof will be omitted below.

The output interface 510 may output a variety of information processed by the processor 120. The output interface 120 may include a visual output module, such as a display, a voice output module, such as a speaker, or a haptic module configured to output a vibration or tactile sensation. For example, the output interface 510 may output contact pressure guide information, a component estimation result, and the like, that are generated by the processor 120.

The storage 520 may store various information related to component estimation. For example, the storage 520 may store information on the user's characteristics, such as the user's age, gender, health status, etc., light source operating conditions, and the like. In addition, the storage 520 may store information on a component estimated value, or the like, generated by the processor 120. The storage 520 may include a storage medium, such as a flash memory type, a hard disk type, a multimedia card micro type, a card type memory (e.g., a secure digital (SD) or eXtreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, an optical disk, and the like, but is not limited thereto.

The communication interface 530 may establish a wired or wireless communication connection with an external device to receive various types of information related to component estimation. The external device may include an information processing device, such as a smartphone, a tablet personal computer (PC), a desktop computer, a laptop computer, or the like. The communication interface 530 may communicate with the external device by using various wired or wireless communication techniques including Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, the communication techniques are not limited thereto.

FIGS. 6 to 11 are flowcharts illustrating a method of estimating a component of an analyte according to example embodiments. The method of estimating a component according to example embodiments may be performed by the above-described apparatuses 100, 400, and 500 for estimating a component. Estimating of a component is described in detail above, and hence a brief description will be made below.

Figure 6:
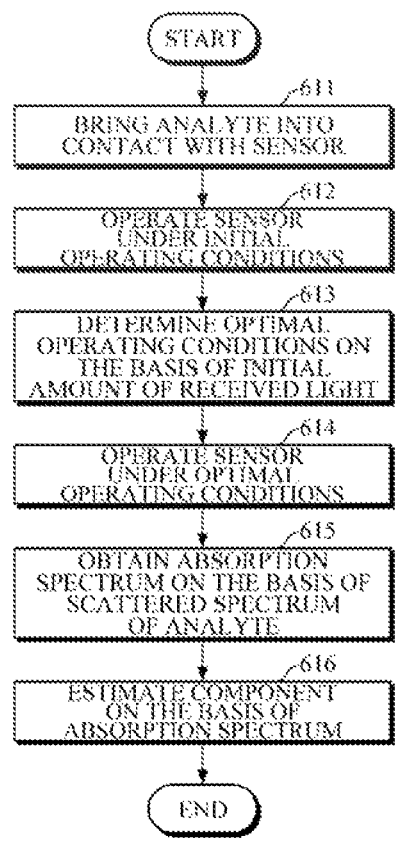
FIGS. 6 to 11 are flowcharts illustrating a method of estimating a component of an analyte according to example embodiments.

Referring to FIG. 6, when an analyte is in contact with the sensor (operation 611), the sensor may be operated under the initial operating conditions (operation 612). In this case, the initial operating conditions of the sensor may be set by using a standard sample having a predetermined reflectivity, and operating conditions that allow the optimal amount of received light to be detected from the standard sample may be set as the initial operating conditions.

Then, when the initial amount of received light is detected from the analyte under the initial operating conditions, optimal operating conditions may be determined based on the detected initial amount of received light, the initial operating conditions, an optimal amount of received light, and the like (operation 613). For example, the optimal operating conditions may be determined through a relationship between a ratio of the optimal amount of received light and the initial amount of received light and a ratio of the optimal operating condition (e.g., exposure time) to be obtained and the initial operating condition (e.g., exposure time).

Then, when the optimal operating conditions are determined in operation 613, the sensor may be operated using the determined optimal operating conditions (operation 614).

Then, when a spectrum is measured from the analyte by operating the sensor under the optimal operating conditions, an absorption spectrum may be obtained on the basis of the measured spectrum (operation 615). For example, the absorption spectrum may be obtained on the basis of a log value of a ratio of the spectrum measured from the analyte and a reference spectrum. In this case, the reference spectrum may be obtained by normalizing the spectrum measured using a standard sample having a predetermined reflectivity into an exposure time, or by obtaining the absorbance of each wavelength corresponding to the optimal exposure time by referring to a lookup table that defines the absorbance of each wavelength for each exposure time.

Then, a component of the analyte may be estimated by using the absorption spectrum obtained in operation 615 (operation 616).

Figure 7:
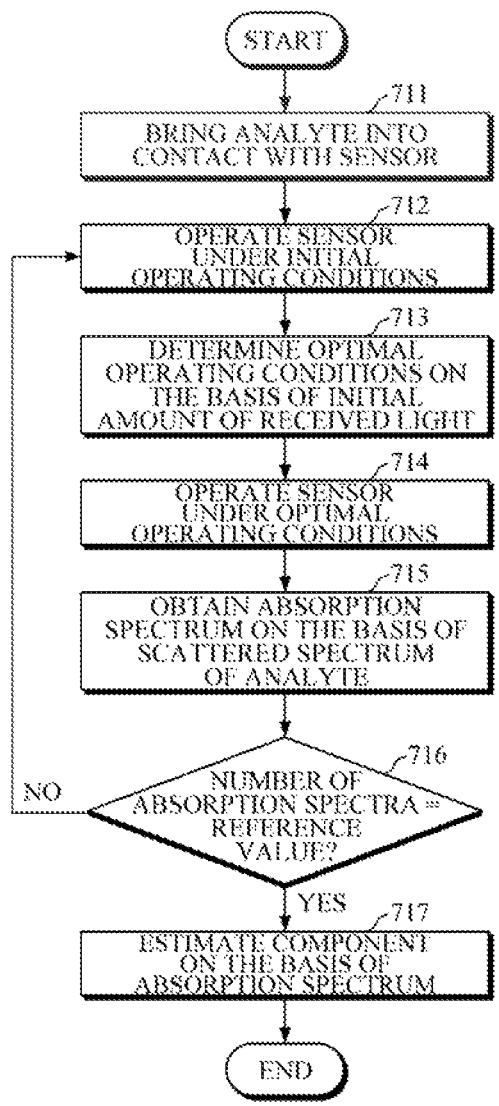

FIG. 7 illustrates an embodiment in which a plurality of absorption spectra are obtained in order to reduce noise caused by blood or skin movement. New optimal operating conditions may be determined each time each absorption spectrum is obtained. As illustrated, when the analyte is in contact with the sensor (operation 711), operation 712 of operating the sensor under the initial operating conditions, operation 713 of determining optimal operating conditions on the basis of an initial amount of received light detected under the initial operating conditions, operation 714 of operating again the sensor using the determined optimal operating conditions, and operation 715 of obtaining an absorption spectrum on the basis of a spectrum measured under the optimal operating conditions may be performed. Then, when the obtained absorption spectrum does not satisfy a predefined reference value (operation 716—NO), operation 712 and the following operations may be repeatedly performed to obtain a plurality of absorption spectra.

Then, when the obtained absorption spectrum does satisfy the predefined reference value (operation 716—YES), a component may be estimated by using the plurality of obtained absorption spectra (operation 717). For example, the component may be estimated by averaging all the absorption spectra or some absorption spectra other than abnormal spectra, or selecting one optimal absorption spectrum. However, the embodiment is not limited thereto.

Figure 8:
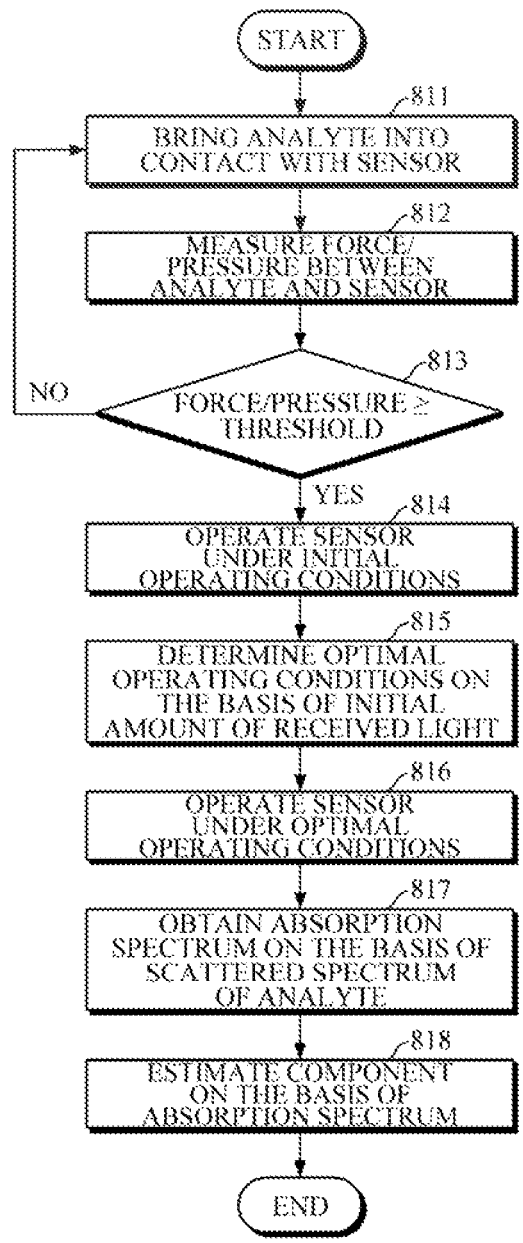

Referring to FIG. 8, when the analyte is in contact with the sensor (operation 811), operation 812 of measuring a force/pressure between the analyte and the sensor may be performed and when the measured force/pressure is less than a preset threshold (operation 813—NO), the operation 811 of bringing the analyte into contact with the sensor may be performed again. At this time, the user may be guided for an appropriate force/pressure. When the measured force/pressure is greater than or equal to the threshold (operation 813—YES), operation 814 of operating the sensor under the initial operating conditions, operation 815 of determining optimal operating conditions on the basis of an initial amount of received light detected under the initial operating conditions, operation 816 of operating the sensor using the determined optimal operating conditions, operation 817 of obtaining an absorption spectrum on the basis of a spectrum measured under the optimal operating conditions, and operation 818 of estimating a component using the absorption spectrum may be performed.

Figure 9:
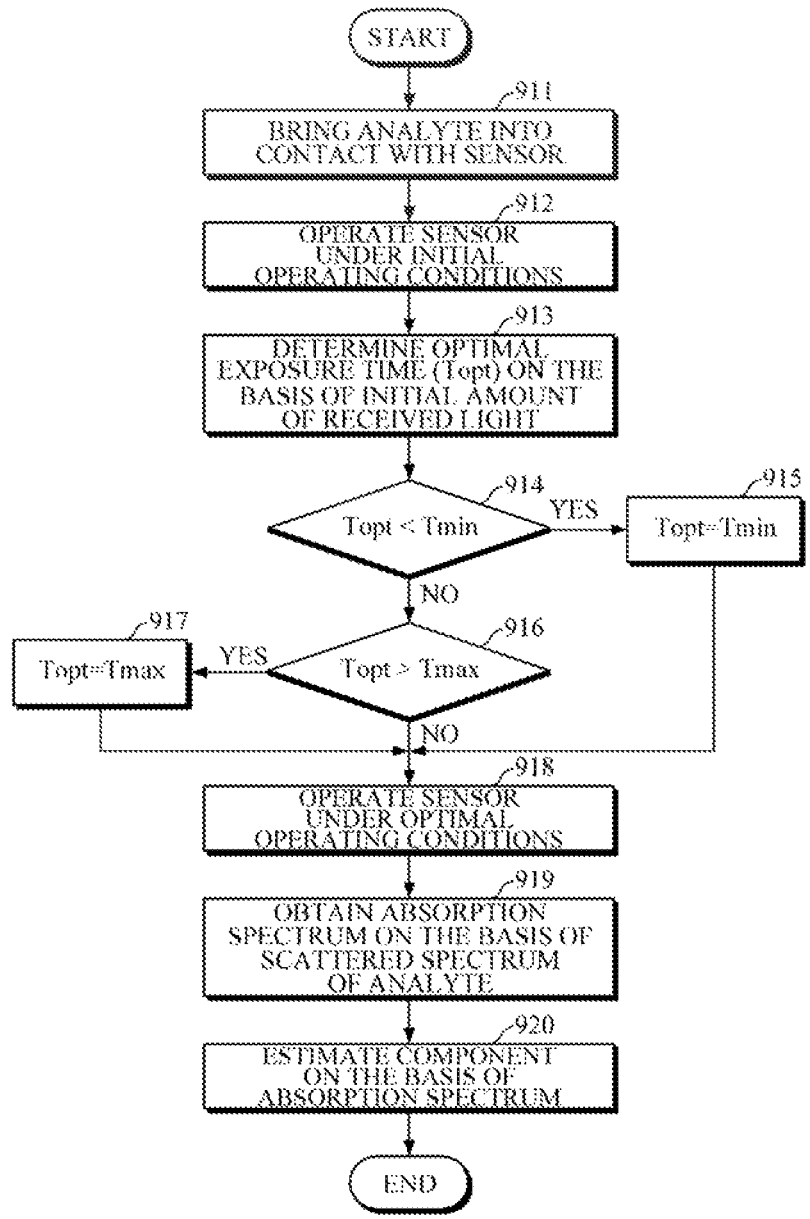
Figure 10:
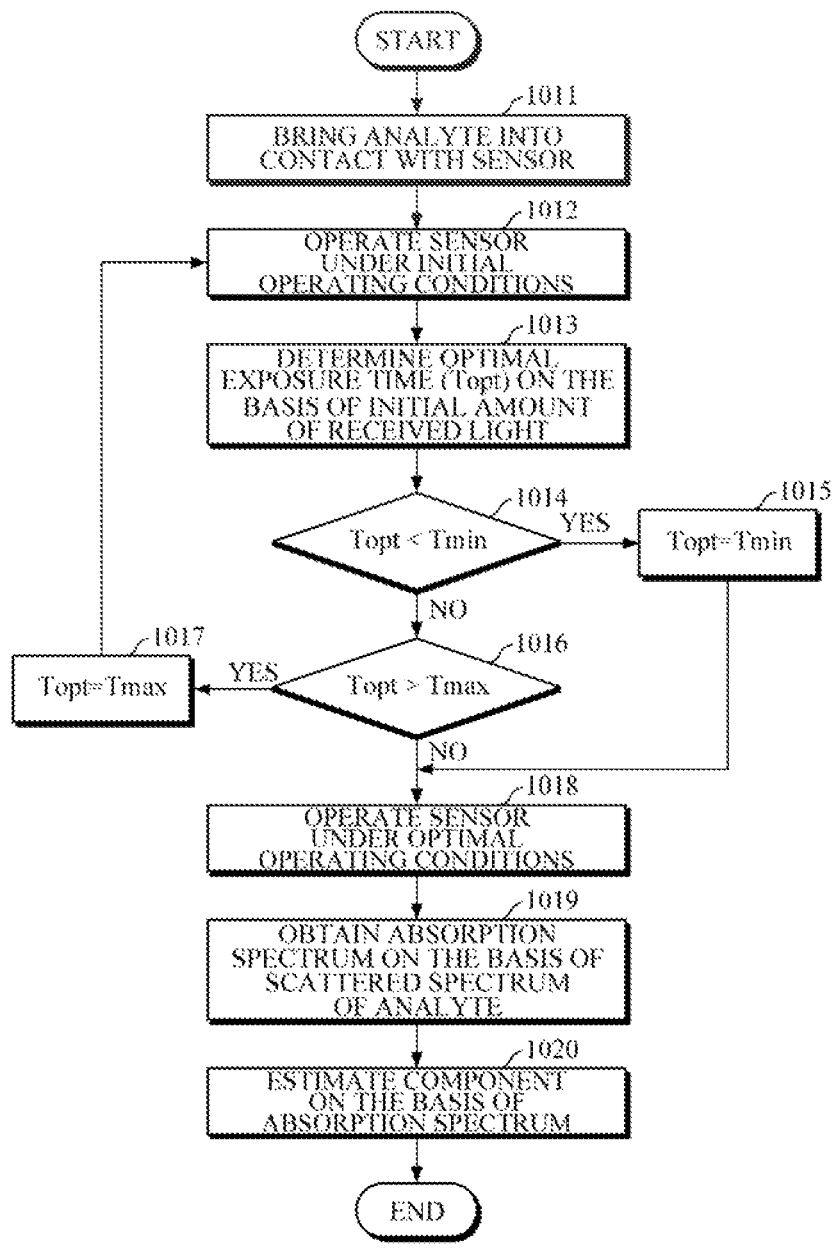
Figure 11:
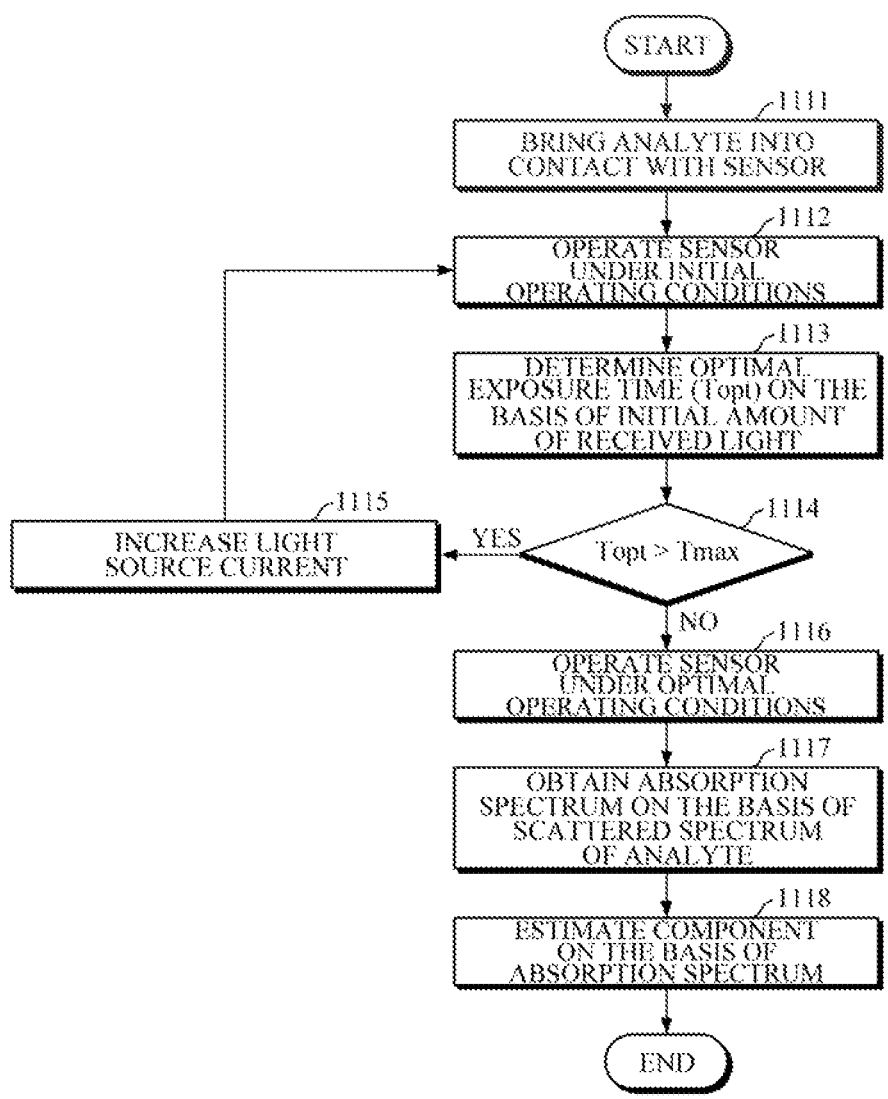

FIGS. 9 to 11 illustrate example embodiments of adjusting an optimal exposure time and/or a light source current among operating conditions of the sensor in the method of estimating a component.

Referring to FIG. 9, when the analyte is in contact with the sensor 911, the sensor may be operated under the initial operating conditions (operation 912), and an optimal exposure time $T_{opt}$ may be determined on the basis of the initial amount of received light detected from the analyte under the initial operating conditions (operation 913).

Then, the optimal exposure time $T_{opt}$ may be compared with a first threshold $T_{min}$ (operation 914), and when the optimal exposure time $T_{opt}$ is less than the first threshold $T_{min}$ (operation 915—YES), the optimal exposure time $T_{opt}$ may be changed to the first threshold $T_{min}$ (operation 915). If the optimal exposure time $T_{opt}$ is greater than or equal to the first threshold $T_{min}$ (operation 914—NO), the optimal exposure time $T_{opt}$ may be compared with a second threshold $T_{max}$ (operation 916), and if the optimal exposure time $T_{opt}$ exceeds the second threshold $T_{max}$ (operation 916—YES), the optimal exposure time $T_{opt}$ may be changed to the second threshold $T_{max}$ (operation 917).

Then, when the optimal operating conditions are determined, the sensor may be operated using the determined optimal operating conditions (operation 918), and when the spectrum of the analyte is measured according to the optimal operating conditions, an absorption spectrum may be obtained based on the measured spectrum (operation 919), and a component of the analyte may be estimated using the obtained absorption spectrum (operation 920).

Referring to FIG. 10, when the analyte is in contact with the sensor (operation 1011), the sensor may be operated under the initial operating conditions (operation 1012), and the optimal exposure time $T_{opt}$ may be determined on the basis of an initial amount of received light detected from the analyte under the initial operating conditions (operation 1013).

Then, the optimal exposure time $T_{opt}$ is compared to a first threshold $T_{min}$ (operation 1014), and when the optimal exposure time $T_{opt}$ is less than the first threshold $T_{min}$ (operation 1014—YES), the optimal exposure time $T_{opt}$ is changed to the first threshold $T_{min}$ (operation 1015), and when the optimal exposure time $T_{opt}$ is greater than or equal to the first threshold $T_{min}$ (operation 1014—NO), the optimal exposure time $T_{opt}$ is compared to a second threshold $T_{max}$ (operation 1016). When the optimal exposure time $T_{opt}$ exceeds the second threshold $T_{max}$, the intensity of incident light of the initial operating conditions may be adjusted by increasing a light source current (operation 1017), and operation 1012 of operating the sensor under the initial operating conditions and the following operations may be repeated.

Then, when the optimal operating conditions are determined, the sensor may be operated using the determined optimal operating conditions (operation 1018), an absorption spectrum may be obtained on the basis of a spectrum measured under the optimal operating conditions (operation 1019), and a component of the analyte may be estimated using the obtained absorption spectrum (operation 1020).

Referring to FIG. 11, when the analyte is in contact with the sensor (operation 1111), the sensor may be operated under the initial operating conditions (operation 1112), and the optimal exposure time $T_{opt}$ may be determined on the basis of the initial amount of received light detected from the analyte under the initial operating conditions (operation 1113). Then, the optimal exposure time $T_{opt}$ may be compared with a second threshold $T_{max}$ (operation 1114), and when the optimal exposure time $T_{opt}$ exceeds the second threshold $T_{max}$ (operation 1114—YES), the intensity of incident light of the initial operating conditions may be adjusted by increasing a light source current (operation 1115), and operation 1112 of operating the sensor under the initial operating conditions and the following operations may be repeated. Then, when the optimal exposure time $T_{opt}$ does not exceed the second threshold $T_{max}$ (operation 1114—NO), the sensor may be operated using the determined optimal operating conditions (operation 1116), an absorption spectrum may be obtained (operation 1117), and a component of the analyte may be estimated using the obtained absorption spectrum (operation 1118).

Figure 12:
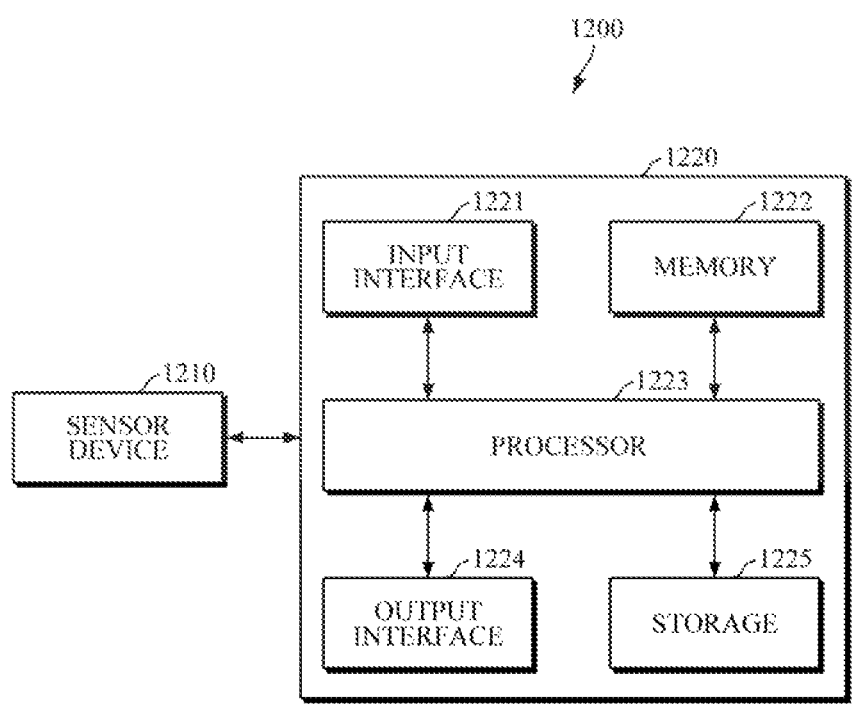
FIG. 12 is a block diagram illustrating an electronic device according to an example embodiment.
Figure 13:
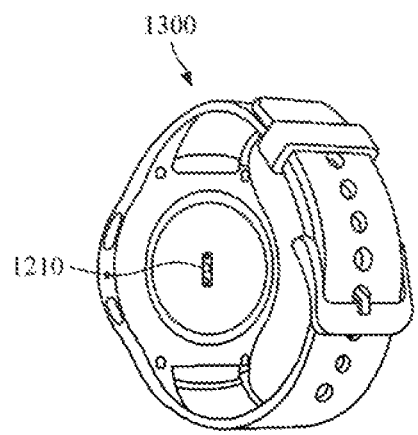
FIGS. 13 to 15 are diagrams illustrating a structure of an electronic device according to example embodiments.
Figure 14:
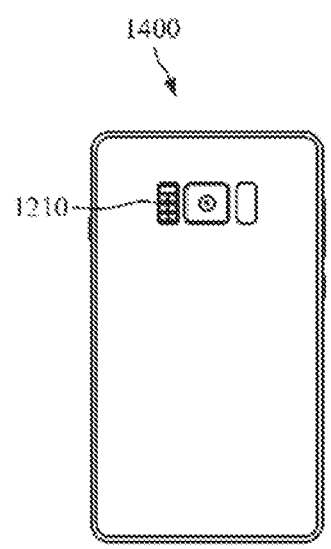
Figure 15:
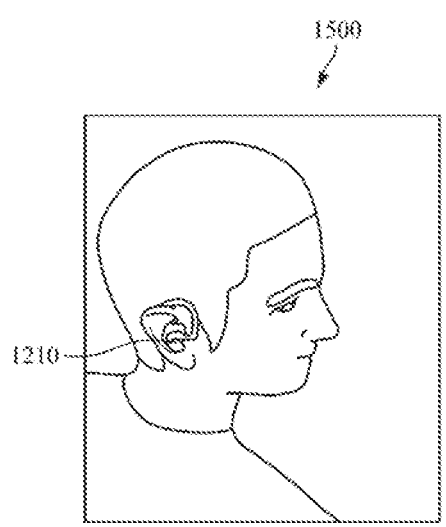

FIG. 12 is a block diagram illustrating an electronic device according to an example embodiment. FIGS. 13 to 15 are diagrams illustrating a structure of an electronic device according to example embodiments.

Referring to FIG. 12, the electronic device 1200 may include a sensor device 1210 and an estimation apparatus 1220 for estimating an in vivo component of a user by using a spectrum measured by the sensor device 1210. Here, the electronic device 1200 may be a wearable device such as, for example, a smart watch, a smart band, smart glasses, a smart earphone, a smart ring, a smart patch, a smart necklace, or a smartphone. Other examples of the electronic device 1200 may include home appliances and various Internet of Things (IoT) devices (e.g., a home IoT device, etc.). However, the electronic device 1200 is not limited to the above examples, and may be a special medical device designed for use in medical institutions.

The sensor device 1210 and the estimation apparatus 1220 of the electronic device 1200 may be integrally mounted in a main body of the illustrated specific device, or may be distributed and mounted in two or more devices. For example, the sensor device 1210 and the estimation device 1220 may be mounted in one smartphone. Alternatively, the sensor device 1210 may be mounted in a smart earphone, the estimation apparatus 1220 may be mounted in a smartphone or smart watch, and a component may be estimated by transmitting and receiving data between the sensor device 1210 and the estimation device 1220 through wired or wireless communication.

The sensor device 1210 may include a light source and a detector, and may further include a communication interface when the sensor device 1210 and the estimation apparatus 1220 are distributed and mounted in different main bodies. The light source may include one or more light emitters, such as LEDs, and the detector may include a photodiode, a photodiode array, a spectrometer, and the like.

The estimation device 1220 may include an input interface 1221, a memory 1222, a processor 1223, an output interface 1224, and a communication interface 1225.

The input interface 1221 may receive a command and/or data to be used in each component of the electronic device 1200 from a user, or the like. The input interface 1221 may include a microphone, a mouse, a keyboard, and/or a digital pen (e.g., a stylus pen).

The memory 1222 may store operating conditions for operating the sensor device 1210 and various data for usage by other components of the electronic device 1200 such as, for example, input data and/or output data for software and related commands, and the like. The memory 1222 may include volatile memory and/or nonvolatile memory.

The processor 1223 may control the components of the electronic device 1220 connected to the processor 1223 by executing the program stored in the memory 1222, and may perform various data processing or operations. The processor 1223 may include a main processor, such as a central processing unit and an application processor, and an auxiliary processor that can be operated independently of, or together with, the main processor such as, for example, a graphic processing unit, an image signal processor, a sensor hub processor, a communication processor, or the like. The processor 1223 may transmit a control signal to the sensor device 1210 according to a user request for estimating the concentration of an analyte, and may estimate a component using a spectrum received from the sensor device 1210.

The output interface 1224 may output data generated or processed by the electronic device 1200 in a visual/non-visual manner. The output interface 1224 may include a sound output device, a display device, an audio module, and/or a haptic module.

The sound output device may output an audio signal external to the electronic device 1200. The sound output device may include a speaker and/or a receiver. The speaker may be used for general purposes, such as playing multimedia or recording and playing, and the receiver may be used for call receiving purposes. The receiver may be formed integrally or separately from the speaker.

The display device may visually provide information to the outside of the electronic device 1200. The display device may include, for example, a display, a hologram device, or a projector and control circuitry to control a corresponding one of the display, hologram device, and projector. The display device may include touch circuitry adapted to detect a touch, or sensor circuitry (e.g., a pressure sensor) adapted to measure the intensity of force incurred by the touch.

The audio module may convert a sound into an electrical signal and vice versa. The audio module may obtain the sound via an input device, or output the sound via the sound output device and/or a speaker and/or a headphone of another electronic device directly or wirelessly connected to the electronic device 1200.

The haptic module may convert an electrical signal into a mechanical stimulus (e.g., a vibration or a movement) or electrical stimulus which may be recognized by a user via his/her tactile sensation or kinesthetic sensation. The haptic module may include a motor, a piezoelectric element, or an electric stimulator.

The communication interface 1225 may support establishing a direct (e.g., wired) communication channel and/or a wireless communication channel between the electronic device 1200 and another external electronic device or a server present within a network environment and performing communication via the established communication channel. The communication interface 1225 may include one or more communication processors that are operable independently of the processor 1223 and supports a direct communication or a wireless communication. The communication interface 1225 may include a wireless communication module (e.g., a cellular communication module, a short-range wireless communication module, or a global navigation satellite system (GNSS) communication module) and/or a wired communication module (e.g., a local area network (LAN) communication module or a power line communication (PLC) module). These various types of communication modules may be implemented as a single chip, or may be implemented as multiple chips separate from each other. The wireless communication module may identify and authenticate the electronic device 1200 in a communication network using subscriber information (e.g., international mobile subscriber identity (IMSI)) stored in a subscriber identification module.

In addition, the electronic device 1200 may further include an interface, an antenna module, a power management module, a camera module, a battery, or the like.

The interface may support one or more specified protocols to be used for the electronic device 1200 to be connected to another electronic device directly or wirelessly. The interface may include a high definition multimedia interface (HDMI), a universal serial bus (USB) interface, a secure digital (SD) card interface, and/or an audio interface, but is not limited thereto.

The antenna module may transmit or receive a signal or power externally from the electronic device 1200. The antenna may include a radiating element composed of a conductive material or a conductive pattern formed in or on a substrate (e.g., a printed circuit board (PCB)). The antenna module may include a single antenna or a plurality of antennas. When a plurality of antennas are included, an antenna appropriate for a communication scheme used in the communication network may be selected by the communication interface 1225 from the plurality of antennas. The signal and/or the power may be transmitted or received between the communication interface 1225 and another electronic device via the selected antenna. Another component (e.g., a radio frequency integrated circuit (RFIC)) other than the antenna may be additionally formed as part of the antenna module. At least some of the above-described components may be connected mutually and communicate commands or data therebetween via an inter-peripheral communication scheme (e.g., a bus, general purpose input and output (GPIO), serial peripheral interface (SPI), or mobile industry processor interface (MIPI)).

Here, other electronic devices may be devices of a same type as, or a different type, from the electronic device. All or some of operations to be executed by the electronic device 1200 may be executed by one or more of the other electronic devices. For example, if the electronic device 1200 should perform a function or a service, the electronic device 1200, instead of executing the function or the service, may request the one or more other electronic devices to perform at least part of the function or the service. The one or more other electronic devices receiving the request may perform an additional function or an additional service related to the request, and transfer an outcome of the performing to the electronic device 1200. To this end, a cloud computing, distributed computing, or client-server computing technology may be used.

The camera module may capture a still image or moving images. The camera module may include one or more lenses, image sensors, image signal processors, and/or flashes. A lens assembly included in the camera module may collect light emitted from an object whose image is to be taken.

The power management module may manage power supplied to the electronic device 1200. The power management module may be implemented as at least part of a power management integrated circuit (PMIC).

The battery may supply power to the components of the electronic device 1200. The battery may include a primary cell which is not rechargeable, a secondary cell which is rechargeable, or a fuel cell.

FIGS. 13 to 15 are diagrams illustrating exemplary structures of an electronic device in which an apparatus for estimating a component is mounted.

Referring to FIG. 13, the electronic device 1200 may be implemented as a watch-type wearable device 1300, and may include a main body and a wrist strap. A display may be provided on the front of the main body, and display various application screens including time information, received message information, and the like. A sensor device 1210 may be disposed on the rear of the main body, and may measure a spectrum for estimating a component, such as an antioxidant index, or the like.

Referring to FIG. 14, the electronic device 1200 may be implemented as a mobile device 1400, such as a smartphone.

The mobile device 1400 may include a housing and a display panel. The housing may form an exterior of the mobile device 1400. A display panel and cover glass may be sequentially disposed on a first surface of the housing and the display panel may be exposed to the outside through the cover glass. The sensor device 1210, the camera module and/or an infrared sensor may be disposed on a second surface of the housing. When the user runs an application, or the like, mounted in the mobile device 1400 to request for component information of an analyte, a component of the analyte may be estimated using the sensor device 1210 and the component estimation information may be provided to the user through an image or sound.

Referring to FIG. 15, the electronic device 1200 may also be implemented as an ear-wearable device 1500.

The ear-wearable device 1500 may include a main body and an ear strap. The user may wear the ear strap by hanging in on the auricle. The ear strap may be omitted depending on the shape of the ear-wearable device 1500. The main body may be inserted into the user's external auditory meatus. The sensor device 1210 may be mounted in the main body. Then, the ear-wearable device 1500 may provide a component estimation result to the user through sound or transmit the component estimation result to an external device, such as a mobile device, a tablet device, or a PC, through a communication module provided inside the main body.

The current embodiments can be implemented by computer readable code stored on a non-transitory computer readable medium. Code and code segments constituting the computer program can be inferred by a computer programmer skilled in the art. The computer readable medium includes all types of recording media in which computer readable data are stored. Examples of the computer readable medium include a ROM, a RAM, a CD-ROM, a magnetic tape, a floppy disk, and an optical data storage. Further, the computer readable medium may be implemented in the form of a carrier wave such as Internet transmission. In addition, the computer readable medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for estimating a component of an analyte, the apparatus comprising:
 a sensor including a light source configured to emit light to the analyte, and a detector configured to measure a spectrum of light reflected from the analyte; and
 a processor configured to:
  based on an initial amount of received light being obtained from the analyte by operating the sensor under initial operating conditions, determine optimal operating conditions based on the initial amount of received light and the initial operating conditions;
  based on a spectrum being measured from the analyte by operating the sensor under the optimal operating conditions, estimate the component of the analyte based on the spectrum; and
  obtain an absorption spectrum of the analyte based on the spectrum and a reference spectrum.

2. The apparatus of claim 1, wherein the initial operating conditions of the sensor comprise at least one of an intensity of incident light, a gain, an exposure time, or an aperture size.

3. The apparatus of claim 1, wherein the initial operating conditions are set such that a preset optimal amount of received light is detected from a standard sample having a predetermined reflectivity.

4. The apparatus of claim 3, wherein the predetermined reflectivity comprises at least one of an average reflectivity and a maximum reflectivity of the analyte.

5. The apparatus of claim 1, wherein the processor is further configured to determine the optimal operating conditions based on a ratio of the initial amount of received light to a preset optimal amount of received light and the initial operating conditions.

6. The apparatus of claim 5, wherein the processor is further configured to change the optimal operating conditions to a first threshold based on the optimal operating conditions being less than the first threshold.

7. The apparatus of claim 5, wherein the processor is further configured to change the optimal operating conditions to a second threshold based on the optimal operating conditions exceeding the second threshold.

8. The apparatus of claim 5, wherein the processor is further configured to, based on the optimal operating conditions exceeding the second threshold, repeatedly obtain an initial amount of received light by operating the sensor after increasing a light source current among the initial operating conditions.

9. The apparatus of claim 1, further comprising a force sensor or a pressure sensor configured to measure a force or a pressure applied between the analyte and the sensor,
wherein the processor is further configured to operate the sensor based on the force or the pressure being greater than or equal to a predetermined threshold.

10. The apparatus of claim 9, wherein the processor is further configured to control an output interface to output information that guides a user to change the force or the pressure applied between the analyte and the sensor based on the force or the pressure.

11. The apparatus of claim 1, wherein the processor is further configured to obtain the reference spectrum by normalizing a sample spectrum measured using a standard sample having a predetermined reflectivity based on the initial operating conditions and the optimal operating conditions.

12. The apparatus of claim 11, wherein the processor is further configured to normalize the spectrum by multiplying an amount of reflected light of the sample spectrum by a ratio of an exposure time among the optimal operating conditions and an exposure time among the initial operating conditions.

13. The apparatus of claim 1, wherein the processor is further configured to obtain the reference spectrum that corresponds to the optimal operating conditions by referring to a preset lookup table.

14. The apparatus of claim 1, wherein the processor is further configured to estimate the component of the analyte based on the absorption spectrum by using a preset estimation model.

15. The apparatus of claim 1, wherein the component of the analyte comprises at least one of skin carotenoid, blood carotenoid, glucose, urea, lactate, triglyceride, total protein, cholesterol, or ethanol.

16. A method of estimating a component of an analyte, the method comprising:
operating a sensor under preset initial operating conditions;
detecting an initial amount of received light from the analyte under the initial operating conditions;
determining optimal operating conditions based on the initial amount of received light and the initial operating conditions;
measuring a spectrum from the analyte by operating the sensor under the optimal operating conditions; and
estimating the component of the analyte based on the spectrum,
wherein the obtaining of the component of the analyte comprises obtaining a reference spectrum, obtaining an absorption spectrum of the analyte based on the spectrum and the reference spectrum, and estimating the component of the analyte based on the absorption spectrum.

17. The method of claim 16, wherein the initial operating conditions are set such that a preset optimal amount of received light is detected from a standard sample having a predetermined reflectivity.

18. The method of claim 16, wherein the determining of the optimal operating conditions comprises determining the optimal operating conditions based on a ratio of the initial amount of received light to a preset optimal amount of received light and the initial operating conditions.

19. The method of claim 18, wherein the determining of the optimal operating conditions comprises changing the optimal operating conditions to a first threshold based on the determined optimal operating conditions being less than the first threshold.

20. The method of claim 18, wherein the determining of the optimal operating conditions comprises changing the optimal operating conditions to a second threshold based on the determined optimal operating conditions exceeding the second threshold.

21. The method of claim 18, wherein the determining of the optimal operating conditions comprises, based on the determined optimal operating conditions exceeding the second threshold, repeatedly obtaining an initial amount of received light by operating the sensor after increasing a light source current among the initial operating conditions.

22. The method of claim 16, further comprising measuring a force or a pressure applied between the analyte and the sensor,
wherein the operating of the sensor under the initial operating conditions comprises operating the sensor based on the measured is the force or the pressure being greater than or equal to a predetermined threshold.

23. The method of claim 16, wherein the obtaining the reference spectrum comprises obtaining the reference spectrum by normalizing a sample spectrum measured using a standard sample having a predetermined reflectivity based on the initial operating conditions and the optimal operating conditions.

24. The method of claim 16, wherein the obtaining the reference spectrum comprises obtaining the reference spectrum that corresponds to the optimal operating conditions by referring to a preset lookup table.

25. The method of claim 16, wherein the estimating of the component comprises estimating the component of the analyte based on the absorption spectrum by using a preset estimation model.

26. An electronic device comprising:
a main body;
a memory disposed in the main body; and
a processor disposed in the main body and electrically connected to the memory,
wherein the processor is configured to:
operate a sensor device under initial operating conditions stored in the memory based on a request for estimating an antioxidant index being received,
adjust, based on an initial amount of received light being obtained from skin of a user, at least one of a light exposure time and a light source current among operating conditions of the sensor device based on the initial amount of received light, obtain a spectrum from skin of the user by operating the sensor device under adjusted operating conditions, and estimate the antioxidant index based on the spectrum wherein the processor is further configured to adjust the light exposure time based on a ratio of the initial amount of received light to a preset optimal amount of received light and the light exposure time of the initial operating conditions.

27. The electronic device of claim 26, wherein the electronic device comprises at least one of a smart watch, a smart band, smart glasses, a smart earphone, a smart ring, a smart patch, a smart necklace, or a smartphone.

28. The electronic device of claim 26, wherein the processor is further configured to set the initial operating conditions such that a preset optimal amount of received light is detected from a standard sample having a predetermined reflectivity.

29. The electronic device of claim 26, wherein the processor is further configured to, based on an adjusted light exposure time being less than a first threshold, change the light exposure time to the first threshold, and based on the adjusted light exposure time exceeding a second threshold, change the light exposure time to the second threshold, or repeatedly obtain the initial amount of received light and adjust operating conditions of a light source after increasing the light source current.

30. The electronic device of claim 26, further comprising an output interface, disposed in the main body, including at least one of a sound module and a display that outputs a processing result of the processor.

31. An apparatus for estimating a component of an analyte, the apparatus comprising:

a sensor including a light source configured to emit light to the analyte, and a detector configured to measure a spectrum of light reflected from the analyte; and a processor configured to:

based on an initial amount of received light being obtained from the analyte by operating the sensor under first operating conditions, determine second operating conditions based on the initial amount of received light and the first operating conditions;

based on a spectrum being measured from the analyte by operating the sensor under the second operating conditions, estimate the component of the analyte based on the spectrum, and obtain an absorption spectrum of the analyte based on the spectrum and a reference spectrum.

* * * * *